(12) United States Patent
Sackler et al.

(10) Patent No.: US 6,699,908 B2
(45) Date of Patent: Mar. 2, 2004

(54) METHODS FOR PROVIDING SAFE LOCAL ANESTHESIA

(75) Inventors: Richard S. Sackler, Greenwich, CT (US); Paul D. Goldenheim, Wilton, CT (US); Mark Chasin, Manalapan, NJ (US); Ronald M. Burch, Wilton, CT (US); Robert F. Reder, Greenwich, CT (US); Joseph Tigner, New Milford, CT (US)

(73) Assignee: Euro-Celtique, S.A., Luxembourg (LU)

( * ) Notice: Subject to any disclaimer, the term of this patent is extended or adjusted under 35 U.S.C. 154(b) by 136 days.

(21) Appl. No.: 09/963,256

(22) Filed: Sep. 26, 2001

(65) Prior Publication Data

US 2002/0114835 A1 Aug. 22, 2002

Related U.S. Application Data

(63) Continuation of application No. 09/435,794, filed on Nov. 8, 1999, now abandoned, which is a continuation of application No. 08/881,535, filed on Jun. 24, 1997, now abandoned.
(60) Provisional application No. 60/020,315, filed on Jun. 24, 1996.

(51) Int. Cl.[7] ............................................. A61K 31/195
(52) U.S. Cl. ....................................... 514/563; 514/818
(58) Field of Search ................................. 514/563, 818

(56) References Cited

U.S. PATENT DOCUMENTS

| | | |
|---|---|---|
| 2,174,796 A | 10/1939 | Luzzi ............................ 32/34 |
| 2,835,628 A | 5/1958 | Saffir ........................... 167/84 |
| 3,185,625 A | 5/1965 | Brown .......................... 167/82 |
| 3,337,400 A | 8/1967 | Smith ........................... 167/52 |
| 3,507,952 A | 4/1970 | Rednick et al. ............... 424/22 |
| 3,535,419 A | 10/1970 | Siegrist et al. ................ 424/22 |
| 3,736,646 A | 6/1973 | Schmitt et al. ............... 29/458 |
| 3,755,558 A | 8/1973 | Scribner ....................... 424/47 |
| 3,773,919 A | 11/1973 | Boswell, et al. .............. 424/19 |
| 3,844,285 A | 10/1974 | Laby ........................... 128/260 |
| 3,887,699 A | 6/1975 | Yolles .......................... 424/19 |
| 3,943,063 A | 3/1976 | Morishita et al. ........... 252/316 |
| 3,972,995 A | 8/1976 | Tsuk et al. .................... 424/28 |
| 3,972,999 A | 8/1976 | Tsuk ............................. 424/78 |
| 3,976,071 A | 8/1976 | Sadek ......................... 128/260 |
| 3,991,766 A | 11/1976 | Schmitt et al. ........... 128/335.5 |
| 4,001,388 A | 1/1977 | Shell ............................ 424/14 |
| 4,011,312 A | 3/1977 | Reuter et al. ................. 424/78 |
| 4,034,758 A | 7/1977 | Theeuwes ................... 128/260 |
| 4,039,653 A | 8/1977 | DeFoney et al. ............. 424/19 |
| 4,070,347 A | 1/1978 | Schmitt ................... 260/77.5 D |
| 4,076,798 A | 2/1978 | Casey et al. .................. 424/22 |
| 4,089,800 A | 5/1978 | Temple ....................... 252/316 |
| 4,093,709 A | 6/1978 | Choi et al. .................... 424/19 |
| 4,118,470 A | 10/1978 | Casey et al. .................. 424/19 |
| 4,131,648 A | 12/1978 | Choi et al. .................... 424/22 |
| 4,138,344 A | 2/1979 | Choi et al. ...................... 252/1 |
| 4,144,317 A | 3/1979 | Higuchi et al. ............... 424/21 |
| 4,164,560 A | 8/1979 | Folkman et al. .............. 424/22 |
| 4,166,107 A | 8/1979 | Miller et al. .................. 424/19 |
| 4,166,800 A | 9/1979 | Fong ........................... 252/316 |
| 4,175,326 A | 11/1979 | Goodson ...................... 433/80 |
| 4,226,848 A | 10/1980 | Nagai et al. .................. 424/19 |
| 4,250,163 A | 2/1981 | Nagai et al. .................. 424/14 |
| 4,276,880 A | 7/1981 | Malmin ...................... 128/221 |
| 4,293,539 A | 10/1981 | Ludwig et al. ............... 424/19 |
| 4,321,038 A | 3/1982 | Porteous ..................... 433/136 |
| 4,331,728 A | 5/1982 | Theeuwes et al. ........... 428/215 |
| 4,369,172 A | 1/1983 | Schor et al. .................. 424/19 |
| 4,384,975 A | 5/1983 | Fong ....................... 427/213.36 |
| 4,389,330 A | 6/1983 | Tice et al. ................ 427/213.36 |
| 4,404,183 A | 9/1983 | Kawata et al. ................ 424/19 |
| 4,419,340 A | 12/1983 | Yolles .......................... 424/19 |
| 4,434,153 A | 2/1984 | Urquhart et al. ............. 424/22 |
| 4,479,911 A | 10/1984 | Fong ............................ 264/4.6 |
| 4,530,840 A | 7/1985 | Tice et al. ................... 514/179 |
| 4,542,025 A | 9/1985 | Tice et al. ..................... 424/78 |
| 4,557,925 A | 12/1985 | Lindahl et al. ............... 424/19 |
| 4,568,535 A | 2/1986 | Loesche ....................... 424/19 |
| 4,568,536 A | 2/1986 | Kronenthal et al. .......... 424/22 |
| 4,569,837 A | 2/1986 | Suzuki et al. ................. 424/28 |
| 4,585,651 A | 4/1986 | Beck et al. .................... 424/88 |
| 4,597,960 A | 7/1986 | Cohen ......................... 424/28 |
| 4,622,219 A | 11/1986 | Haynes ........................ 424/38 |
| 4,622,244 A | 11/1986 | Lapka et al. ............. 427/213.32 |
| 4,623,588 A | 11/1986 | Nuwayser et al. ....... 428/402.24 |
| 4,650,665 A | 3/1987 | Kronenthal et al. ........ 424/435 |
| 4,652,441 A | 3/1987 | Okada et al. ................. 424/19 |
| 4,685,883 A | 8/1987 | Jernberg .................... 433/136 |
| 4,713,244 A | 12/1987 | Bawa et al. ................. 424/429 |
| 4,716,203 A | 12/1987 | Casey et al. ................. 525/408 |
| 4,725,442 A | 2/1988 | Haynes ....................... 424/490 |
| 4,735,945 A | 4/1988 | Sakamoto et al. .......... 514/279 |

(List continued on next page.)

FOREIGN PATENT DOCUMENTS

| | | | |
|---|---|---|---|
| CA | 1143289 | 3/1983 | ............ A61K/9/50 |
| DE | 2930248 | 2/1981 | ............ B01J/13/02 |
| EP | 0195906 | 2/1986 | ........... A61K/31/71 |
| EP | 0244118 A1 | 11/1987 | ............ A61K/9/10 |

(List continued on next page.)

OTHER PUBLICATIONS

Jaffe, Howard, "Microencapsulation Process", copy of government–owned invention description, Ser. No.: 943,940, filed Aug. 17, 1978, U.S. Department of Agriculture, Hyattsville, MD, 11 pages.

Algire, Glenn H., et al., "Vascular Reactions of Normal and Malignant Tissues In Vivo. VI.. The Role of Hypotension in the Action of Components of Podophyllin on Transplanted Sarcomas", *Journal of the American Cancer institute*, vol. 14, No. 4, Feb. 1954, pp 879–893.

(List continued on next page.)

*Primary Examiner*—Zohreh Fay
(74) *Attorney, Agent, or Firm*—Davidson, Davidson & Kappel, LLC (57) ABSTRACT

Methods and formulations for inducing substantially safer local anesthesia in a patient are provided. The methods comprise administering, to a patient in need thereof, a substrate containing a local anesthetic and an effective amount of a biocompatible, biodegradable, controlled release material to safely obtain a reversible nerve blockade when implanted or injected in a patient.

27 Claims, 4 Drawing Sheets

U.S. PATENT DOCUMENTS

| | | | | |
|---|---|---|---|---|
| 4,756,907 | A | 7/1988 | Beck et al. | 424/85 |
| 4,757,128 | A | 7/1988 | Domb et al. | 528/271 |
| 4,767,628 | A | 8/1988 | Hutchinson | 424/426 |
| 4,780,320 | A | 10/1988 | Baker | 424/493 |
| 4,789,726 | A | 12/1988 | Hutchinson | 528/354 |
| 4,801,739 | A | 1/1989 | Franz et al. | 560/185 |
| 4,861,627 | A | 8/1989 | Mathiowitz et al. | 427/213.31 |
| 4,874,612 | A | 10/1989 | Deasy | 424/425 |
| 4,882,168 | A | 11/1989 | Casey et al. | 424/468 |
| 4,883,666 | A | 11/1989 | Sabel et al. | 424/422 |
| 4,888,176 | A | 12/1989 | Langer et al. | 424/426 |
| 4,891,225 | A | 1/1990 | Langer et al. | 424/428 |
| 4,892,736 | A | 1/1990 | Goodson | 424/435 |
| 4,906,474 | A | 3/1990 | Langer et al. | 424/428 |
| 4,919,939 | A | 4/1990 | Baker | 424/493 |
| 4,933,182 | A | 6/1990 | Higashi et al. | 424/425 |
| 5,000,886 | A | 3/1991 | Lawter et al. | 264/4.3 |
| 5,004,602 | A | 4/1991 | Hutchinson | 424/78 |
| 5,007,790 | A | 4/1991 | Shell | 424/451 |
| 5,013,553 | A | 5/1991 | Southard et al. | 424/426 |
| 5,019,379 | A | 5/1991 | Domb et al. | 424/78 |
| 5,019,400 | A | 5/1991 | Gombotz et al. | 424/497 |
| 5,032,384 | A | 7/1991 | Yeh et al. | 424/49 |
| 5,061,492 | A | 10/1991 | Okada et al. | 424/401 |
| 5,075,109 | A | 12/1991 | Tice et al. | 424/88 |
| 5,084,267 | A | 1/1992 | Damani | 424/426 |
| 5,100,669 | A | 3/1992 | Hyon et al. | 424/426 |
| 5,114,718 | A | 5/1992 | Damani | 424/422 |
| 5,122,367 | A | 6/1992 | Ron et al. | 424/80 |
| 5,143,661 | A | 9/1992 | Lawter et al. | 264/4.3 |
| 5,188,837 | A | 2/1993 | Domb | 424/450 |
| 5,198,220 | A | 3/1993 | Damani | 424/426 |
| 5,222,529 | A | 6/1993 | Zoltan | 141/4 |
| 5,225,441 | A | 7/1993 | Vogel et al. | 514/557 |
| 5,227,165 | A | 7/1993 | Domb et al. | 424/450 |
| 5,236,355 | A | 8/1993 | Brizzolara et al. | 433/80 |
| 5,244,678 | A | 9/1993 | Legros et al. | 424/450 |
| 5,252,701 | A | 10/1993 | Jarrett et al. | 528/354 |
| 5,264,207 | A | 11/1993 | Bommelaer et al. | 424/69 |
| 5,272,139 | A | 12/1993 | Cary, Jr. | 514/171 |
| 5,292,512 | A | 3/1994 | Schaefer et al. | 424/401 |
| 5,330,452 | A | 7/1994 | Zook | 604/307 |
| 5,401,507 | A | 3/1995 | Lewis | 424/426 |
| 5,407,609 | A | 4/1995 | Tice et al. | 264/46 |
| 5,492,901 | A | 2/1996 | Fabunan | 514/171 |
| 5,540,912 | A | 7/1996 | Roorda et al. | 424/422 |
| 5,543,156 | A | 8/1996 | Roorda et al. | 424/484 |
| 5,618,563 | A | * 4/1997 | Berde et al. | 424/501 |
| 5,650,173 | A | 7/1997 | Ramstack et al. | 424/489 |
| 5,654,008 | A | 8/1997 | Herbert et al. | 424/489 |
| 5,700,485 | A | 12/1997 | Berde et al. | 424/501 |
| 5,747,060 | A | 5/1998 | Sackler et al. | 424/426 |
| 5,885,786 | A | 3/1999 | Cabot | 435/7.21 |
| 5,922,340 | A | 7/1999 | Berde et al. | 424/426 |
| 5,942,241 | A | 8/1999 | Chasin et al. | 424/426 |
| 6,046,187 | A | 4/2000 | Berde et al. | 514/226 |
| 6,197,326 | B1 | 3/2001 | Suzuki et al. | 424/426 |
| 6,214,387 | B1 | 4/2001 | Berde et al. | 424/501 |
| 6,217,911 | B1 | 4/2001 | Vaugn et al. | 424/501 |
| 6,238,702 | B1 | 5/2001 | Berde et al. | 424/489 |
| 6,248,345 | B1 | 6/2001 | Goldenheim et al. | 424/426 |
| 6,426,339 | B1 | 7/2002 | Berde et al. | 514/180 |
| 6,451,335 | B1 | 9/2002 | Goldenheim et al. | 424/426 |

FOREIGN PATENT DOCUMENTS

| | | | | |
|---|---|---|---|---|
| EP | | 0430474 A1 | 6/1991 | A61K/9/70 |
| EP | | 0797988 A2 | 10/1997 | A61K/9/16 |
| FR | | 2592791 | 7/1987 | |
| GB | | 2034182 A | 6/1980 | A61K/9/00 |
| WO | | 9117772 | 11/1991 | A61K/47/30 |
| WO | | 9207555 A1 | 5/1992 | A61K/9/22 |
| WO | | 9215286 | 9/1992 | A61K/9/22 |
| WO | | WO 9215286 A1 | 9/1992 | A61K/9/22 |
| WO | | WO 9320138 A2 | 10/1993 | |
| WO | | WO 9405265 A1 | 3/1994 | A61K/9/20 |
| WO | | 9513799 A1 | 5/1995 | A61K/9/50 |
| WO | | WO 9641616 A1 | 12/1996 | A61K/9/14 |

OTHER PUBLICATIONS

Baguley, Bruce C., et al., "Inhibition of Growth of Colon 38 Adenocarcinoma by Vinblastine and Colchicine: Evidence for a Vascular Mechanism", *Eur. J. Cancer*, vol. 27, No. 4, pp. 482–487 (1991).

Beck, Lee R., et al., "Poly(DL–Lactide–co–glycolide)/Norethisterone Microcapsules: an Injectable Biodegradable Contraceptive", *Biology of Reproduction*, vol. 28, pp. 186–195 (1983).

Bissery, M.C., et al., "A Study of Process Parameters in the Making of Microspheres by the Solvent Evaporation Procedure", EXPO–Congr. Int. Technol. Pharm., 3rd, pp. 233–239 (1983).

Bodmeier, R., et al., "Solvent selection in the preparation of poly(DL–lactide) microspheres prepared by the solvent evaporation method", *International Journal of Pharmaceutics*, vol. 43, pp. 179–186, (1988).

Bodmeier, R., et al., "Polylactic acid microspheres containing quinidine base and quinidine sulphate prepared by the solvent evaporation technique. II. Some process parameters influencing the preparation and properties of microspheres", *J. Microencapsulation*, vol. 4, No. 4, pp. 289–297 (1987).

Hill, S.A., et al., "Vinca Alkaloids: Anti–vascular Effects in a Murine Tumour", *Euro. J. Cancer*, vol. 29A, No. 9, pp. 1320–1324 (1993).

Jalil, R., et al., "Microencapsulation using poly(L–lactic acid) I: Microcapsule properties affected by the preparative technique", *J. Microencapsul.*, vol. 6, No. 4, pp. 473–484 (Oct–Dec) (1989).

Lin, Shan–Yang, et al., "Insulin Controlled–release Microcapsules to Prolong the Hypoglycemic Effect in Diabetic Rats", *Biomat. Art. Cells, Art. Org.*, vol. 16, No. 4, pp. 815–828 (1988).

Lin, Shan–Yang, et al., "Microencapsulation and controlled release of insulin from polylactic acid microcapsules", *Biomat. Med. Dev., Art. Org.*, vol. 13, Nos. 3&4, pp. 187–201 (1985–86).

Mathiowitz, E., et al., "Polyanhydride Microspheres as Drug Carriers. II. Microencapsulation by Solvent Removal", *Journal of Applied Polymer Science*, vol. 35, pp. 755–774 (1988).

Splenhauer, G., et al., "In vitro and in vivo degradation of poly(D,L lactide/glycolide) type microspheres made by solvent evaporation method", *Biomaterials*, vol. 10, pp. 557–563 (Oct. 1989).

Thies, Curt, "Microcapsules as Drug Devices Systems", *Crit. Rev. Biomed. Eng.*, vol. 8, Issue 4, pp. 335–383 (1982).

Windholz, M., et al. *The Merck Index*, 10th Edition, p. 37, Abstract #225 (1983).

Thomas R. Tice, et al. Biodegradation of Microcapsules and Biomedical Devices Prepared with Resorbable Polyesters, Southern Research Institute, University of Alabama. (pp. 21–23).

William T. Buchanan, et al. Systemic Effects of epinephrine–impregnated retraction cord in fixed partial denture prosthodontics, JADA, vol. 104, Apr. 1982.

David B. Masters, et al., Sustained Local Anesthetic Release from Bioerodible Polymer Matrices: A Potential Method for Prolonged Regional Anesthesia, Pharmaceutical Research, vol. 10, No. 10, pp. 1527–32,1993.

N.H. Shah, et al., A biodegradable injectable implant for delivering micro and macromolecules using poly (lactic–co–glycolic) acid (PLGA) copolymers, Journal of Controlled Release, 27 (1993) 139–147.

D.L. Williams, Microencapsulated Local Anesthetics, Proc. Int Symp. Rel Bioact Mater, 11:69–070 (1984).

Journal of Dental Research, IADR Abstract Papers, vol. 61, pp. 860 and 861, Mar. 1982.

Richard L. Dunn, et al., Monolithic Fibers for Controlled Delivery of Tetracycline, Southern Research Institute. (pp. 157–159).

Thomas R. Tice, Controlled Release of Ampicillin and Gentamicin from Biodegradable Microcapsules, Southern Research Institute.

Roland Bodmeier, et al., Polylactic microspheres containing quinidine base and quinidine sulphate prepared by the solvent evaporation method. III. Morphology of the microspheres during dissolution studies, J. Microencapsulation, vol. 5, No. 4, pp. 323–330, 1988.

Marshall Devor, et al., Corticosteroids Suppress Ectopic Neural Discharge Originating in Experimental Neuromas, Pain, 22 pp. 127–137, (1985).

G. McCleane, M.D., et al., The addition of triamcinolone acetonide to bupivacaine has no effect on the quality of analgesia produced by ilioinguinal nerve block, Anaesthesia, vol. 49, pp. 819–820, 1994.

Naoki Wakiyama, et al., Influence of physiochemical properties of polylactic acid on the characteristics and in vitro release patterns of polylactic acid microspheres containing local anesthetics, Chem. Pharm. Bull, 30(7), pp. 2621–2628, 1982.

Duncan H. Haynes, Ph.D., et al., Ultra–long duration Local Anesthesia Produced by Injection Lecithin–coated Methoxyflurane Microdroplets, Anesthesiology, 63:490–499, 1985.

Berde, C.B., et al., "Sustained Release of Dibucaine from a Biodegradable Polymer Matrix: A Potential Method for Prolonged Neural Blockade", Abstracts of Scientific Papers, 1990 Annual Meeting, Amer. Soc. Anesthesiologists, 73:A776 (Sep. 1990).

Edelman, Elazer R., et al., "Optimization of release from magnetically controlled polymeric drug release devices", Biomaterials, 14(8):621–626 (1993).

Masters, et al., Abstract No. 94.3, "Prolonged Sciatic Nerve Blockade Using Sustained Release of Veratridine From a Biodegradable Polymer Matrix", Soc. Neurosci. Abstr., 18:200 (1992).

Fong, Jones W., et al., "Evaluation of biodegradable microspheres prepared by a solvent evaporation process using sodium oleate as emulsifier", Journal of Controlled Release, 3:119–130 (1986).

Fong, J.W., "Microencapsulation by Solvent Evaporation and Organic Phase Separation Processes," pp. 81–108, chapter 5 from Controlled Release Systems: Fabrication Technology, Ed. Dean Hsieh, Ph.D., vol. 1.

Masters, David B., et al., "Prolonged Regional Nerve Blockade by Controlled Release of Local Anesthesia from a Biodegradable Polymer Matrix", Anesthesiology, 79:340–346 (1993).

Miyazaki, S., et al., "External control of drug release: controlled release of insulin from a hyrophilic polymer implant by ultrasound irradiation in diabetic rats", J. Pharm. Pharmacol., 40:716–717 (1988).

Sato, T., et al., "Porous Biodegradable Microspheres for Controlled Drug Delivery. I. Assessment of Processing Conditions and Solvent Removal Techniques", Pharmaceutical Research, 5:21–30 (1988).

Schneider, Markus, M.D., et al., "A Preferential Inhibition of Impulses in C–fibers of the Rabbit Vagus Nerve by Veratridine, an Activator of Sodium Channels", Anesthesiology, 74:270–280 (1991).

Tice, Thomas R., et al., "Preparation of Injectable Controlled–Release Microcapsules by a Solvent–Evaporation Process", Journal of Controlled Release, 2:343–352 (1985).

Wakiyama, Naoki, et al., "Preparation and Evaluation in Vitro and in Vivo of Polylactic Acid Microspheres containing Dibucaine", Chem. Pharm. Bull, 30:3719–3727 (1982).

Duncan, et al., "Treatment of Upper Extremity Reflex Sympathetic Dystrophy with Joint Stiffness Using Sympatholytic Bier Blocks and Manipulation" Orthopedics 11(6), pp. 883–886, (1988).

Flanagan, et al., "Intra–articular injection for pain relief in patients awaiting hip replacement", Ann. Royal Coll. Surg. Eng., vol. 70, pp 156–157 (1988).

Glasser, et al., "The perioperative use of corticosteroids and bupivacaine in the management of lumbar disc disease", J. Neurosurg., vol. 78, pp. 383–387, (1993).

Guttu, et al., "Delayed Healing of Muscle After Injection of Bupivacaine and Steroid", Annals of Dentistry, 49:5–8, (1990).

Hall, et al., "Acute effects of intravenous glucocorticoid on cat spinal motor neuron electrical properties", Brain Research, vol. 240, pp. 186–190, (1982).

Sandrock and Warfield, "Epidural Steroids and Facet Injections", Ch. 29 Principles and Practice of Pain Management, Warfield, C.A., editor (McGraw–Hill, Inc. 1993).

Waldman, et al., "The Relief of Body Wall Pain Secondary to Malignant Hepatic Metastases by Intercostal Nerve Block with Bupivacaine and Methylprednisolone", J. Pain Symptom Management, 3(1), 39–43 (1988), (see in particular p. 42, column 2).

Bonica, John J. and F. Peter Buckley, "Regional Analgesiawith Local Anesthetics", The Management of Pain II; pp. 1883–1966, (1990), Lea & Febiger (Eds.) Second Edition.

Lewis, D.H., et al., "The Use of In Vitro Release Methods to Guide the Development of Controlled–Release Formulations", 9th International Symposium on Controlled Release of Bioactive Materials, Sponsored by Controlled Release Society, Inc., pp. 61–64.

Masters, D.B., et al., Biochemical and Histological Effects of Prolonged Sciatic Nerve Blockade with Bupivacaine Using a Biodegradable Polymer Matrix, vol. 75:A680, (1991).

Devor, et al., 1983, "Axoplasmic Transport Block Reduces Ectopic Impulse Generation in Injured Peripheral Nerves", pp. 73–85.

Schnebel, et al., "The Use of Oral Colchicine for Low–Back Pain", 1987, pp. 354–357.

March, et al., "Biodegradable Microspheres Containing a Colchicine Analogue Inhibit DNA Synthesis in Vascular Smooth Muscle Cells", 1994, pp. 1929–1933.

CA 125:104914, Joanne Curley, et al., "Prolonged regional nerve blockade: Injectable biodegradable bupivacaine/polyester microspheres".

Jean–Marc Malinovsky, et al., "Motor and Blood Pressures Effects of Epidural Sustained–Release Bupivacaine from Polymer Microspheres: A Dose–Response Study in Rabbits", Anesth Analg 1995, 81:519–24.

L.S. Goodman, et al., "The Pharmacological Basis of Therapeutics", Fourth Edition, 1970, The MacMillan Co., p. 372. Vol. IA "Drug Information for the Health Care Professional", USP DI, 1989, Ninth Edition, Anesthetics (Mucosal–Local), pp. 183–184; 196–97; 201–03.

Setterstrom, Tice, Lewis and Meyers, "Controlled Release of Antibiotics from Biodegradable Microcapsules fro Wound Infection Control", U.S. Army Institute of Dental Research, (1982), 12 pages.

Abstract: Archer DR, et al., "Changes in slow axonal transport of tubulin induced by local application of colchicine to rabbit vagus nerve", Acta Physiol Scand Jan. 1994 150(1):57–65.

Abstract: Le Corre, et al., "Spinal controlled delivery of bupivacaine from DL–lactic acid oligomer microspheres", J. Pharm Sci 1995 Jan. 84(1) 75–78.

Abstract: Gradus–Pizlo, et al., "Local delivery of biodegradable microparticles containing colchicine or a . . . ", J. Am. Coll. Cardiol. Nov. 1995 26(6) 1549–57.

Abstract: Penickova V., et al., "Vinblastin iontophoresis in treating intractable pain", Acta Univ Palacki Olomuc Fac Med 1990 128:37–47.

Abstract: Kantner, et al., Regulatory mechanisms for substance P in the dorsal horn during a nociceptive stimulus: axoplasmic transport vs. electrical activity., Brain Res., Oct. 22, 1986 385(2)282–90.

Abstract: Yamamoto, et al., "Effects of colchicine applied to the colchicine applied . . . constriction", Pain, Nov. 1993, 55(2):227–33.

Nakano et al., "Biodegradable Microspheres for Prolonged Local Anesthia," in *Microspheres and Drug Therapy:Pharmaceutical, Immunological and Medical Aspects*, pp. 327–335, Davis, McVie and Tomlinson, Eds. Elsevier, 1984.

XP–002144657 Li, J. and Yan, S., "Analgesic dilator for use in cervical and uterine operations" (abstract of CN1091041).

Lim, J.–O, et al., Prolonged Sciatic Nerve Blockade II: Local Anesthetic–Polymer Microspheres, Abstract Supplement, Abstracts of Scientific Papers 1995 Annual Meeting of American Society of Anesthesiologists, J. Amer. Soc. Anesth. vol. 83, No. 3A, A810 (1995).

Castillo, et al., "Glucocorticosteroids Prolong Rat Sciatic Nerve Blockade in Vivo from Bupivacaine Microspheres", Anesthesiology, 85:1157–66 (1996).

Kojima et al., "Preparation and Evaluation in Vitro of Polycarbonate Microspheres Containing Local Anesthetics", Chem. Pharm. Bull., 32(7) 2795–2802 (1984).

Physicians Desk Reference, "Marcaine", 51 Edition, pp. 2446–2449 (1997).

Estebe, et al., "Prolongation of Spinal Anesthesia with Bupivacaine–Loaded (DL–Lactide) Microspheres", vol. 81(1) Jul. 1995, pp. 99–103.

Le Corre, et al., "In vitro controlled release kinetics of local anaesthetics from poly(D, L–lactide) and poly(lactide–co–glycolide) microspheres", vol 14 No. 2, pp. 243–255.

Abstract: Bernardo, M.V., et al., "In vitro controlled release of bupivacaine from albumin microspheres and a comatrix formed by microspheres in a poly(lactide–co–glycolide) film"J Microencapsul, Nov–Dec 2000 vol 17 pp. 721–731.

* cited by examiner

METHODS FOR PROVIDING SAFE LOCAL ANESTHESIA

This application is a continuation and claims priority from U.S. patent application Ser. No. 09/435,794, filed Nov. 8, 1999 now abandoned, is a continuation and which claims priority form U.S. patent application Ser. No. 08/881,535, filed Jun. 24, 1997 now abandoned, which claims the benefit of U.S. Provisional Patent Application No. 60/020,315, filed Jun. 24, 1996, all of which are hereby incorporated by reference.

FIELD OF THE INVENTION

The present invention is related to methods for providing local anesthesia with greatly enhanced safety and reduced risk of toxicity. In particular, methods are provided for increasing the safety and reducing the risk of toxic reactions and side effects by the use of biocompatible, biodegradable, controlled release formulations for the administration of local anesthetics in a form that provides greatly enhanced safety.

BACKGROUND OF THE INVENTION

Local anesthetics act to produce a loss of sensation and/or motor function in the localized area of administration in the body. Ideally, a local anesthetic does not cause local tissue irritation and does not cause permanent damage to the nerve tissue to which it is applied, i.e., the local anesthesia should be non-toxic and reversible. It is also desirable for a local anesthetic to have low systemic toxicity, since these agents are ultimately absorbed systemically, where sufficient blood and/or tissue levels can cause cardiac toxicity. Further, there is the possibility that such agents could accidentally be injected into a blood vessel or ingested, greatly increasing the risk of untoward effects.

The art has recognized the need for compositions and methods for providing safe local anesthesia with rapid onset and a reasonably prolonged duration, e.g., up to eight hours of local anesthesia. However, methods and formulations heretofore available for providing local anesthesia, particularly local anesthesia lasting as long as eight hours, place the patient at risk for local and systemic toxic effects, such as an increased risk of neurolysis and tissue necrosis and systemic toxicity due to redistribution of excess locally administered local anesthetic into the general circulation.

The duration of action of a local anesthetic is proportional to the time during which it is in actual contact with the nervous tissues. Consequently, procedures or formulations that maintain localization of the drug at the nerve greatly prolong anesthesia. One approach that has heretofore been employed is to combine a vasoconstrictor agent such as epinephrine with a local anesthetic. However, this approach to increasing potency and/or duration of action is limited by the risk of causing tissue necrosis due to excessive localized vasoconstriction.

Another approach was based on analysis of the structure-activity relationship of the local anesthetic compounds. Structure-activity analysis for local anesthetic compounds indicates that relative increases in hydrophobicity are accompanied by relative increases in the potency and in duration of action of these agents. Unfortunately, relative increases in hydrophobicity also elevate the toxic tissue effects, therefore resulting in no effective improvement in the therapeutic index, i.e., no increase in safety will result from this approach. The most recent example of this approach is Naropin™ (ropivacaine, Astra Pharmaceuticals), which was reported to be a safer (relative to bupivacaine solution) long acting amide local anesthetic for injection. However, one condition for the approval of ropivacaine is that the package insert warn against rapid injection in large doses, since it is expected to share the risk of cardiac arrhythmias, cardiac/circulatory arrests and death if inadvertently injected intravenously (F-D-C Reports—"The Pink Sheet", Dec. 18, 1995). Thus, there remains a need in the art for methods and formulations enhancing the safety of administration of local anesthetics.

Different methods and formulations are known in the art for administration of local anesthetics. For example, U.S. Pat. Nos. 4,725,442 and 4,622,219 (Haynes) are directed to microdroplets of methoxyflurane-containing microdroplets coated with a phospholipid prepared by sonication, which are suitable for intradermal or intravenous injection into a patient for inducing local anesthesia. Such microdroplets are said to provide long-term local anesthesia when injected intradermally, giving a duration of anesthesia considerably longer than the longest acting conventional local anesthetic (bupivacaine).

WO 94/05265 describes improved biodegradable controlled release systems consisting of a polymeric matrix incorporating a local anesthetic for the prolonged administration of the local anesthetic agent. The devices are selected on the basis of their degradation profiles: release of the topical anesthetic in a linear, controlled manner over the period of preferably two weeks and degradation in vivo with a half-life of less than six months, more preferably two weeks, to avoid localized inflammation. The disclosure states that an anti-inflammatory can be incorporated into the polymer with the local anesthetic to reduce encapsulation for optimal access of drug to its site of action. The anti-inflammatories that are said to be useful include steroids such as dexamethasone, cortisone, prednisone, and others routinely administered orally or by injection.

However, methods have not previously been known to provide for safe, regulated administration of a local anesthetic resulting in greatly reduced toxicity and an enhanced therapeutic index to provide both short term and long term sensory and motor anesthesia to a local area of a patient in need of such treatment.

OBJECTS OF THE INVENTION

Accordingly, it is therefore an object of the present invention to provide compositions for providing safe local anesthesia with a substantially reduced risk of toxic reactions and/or untoward side effects.

It is a further object of the present invention to provide methods for providing a safe local anesthesia which effectively controls acute and chronic pain, including post-traumatic and post-operative pain.

SUMMARY OF THE INVENTION

In accordance with the above-mentioned objects and others, the invention is related to the discovery that controlled release local anesthetic formulations prepared, e.g., in the form of injectable microspheres, provide both immediate local anesthesia after administration, and provide greatly enhanced safety. Thus, the controlled release formulations according to the invention release enough local anesthetic, in vivo, to provide a normal onset of local anesthesia. However, in an unexpected benefit, the same controlled release local anesthetic formulations fail to cause the expected toxic results when injected into test animals in what would otherwise be toxic amounts. Thus, the present invention provides methods and compositions for inducing local anesthesia with a substantially reduced risk of untoward toxicity and undesirable effects.

The controlled release formulation can be formed into slabs, pellets, microparticles, microspheres, microcapsules, spheroids and pastes. Preferably, the formulation is in a form suitable for suspension in isotonic saline, physiological buffer or other solution acceptable for injection into a patient.

The invention further provides methods for inducing localized anesthesia by implanting, inserting or injecting a controlled release formulation, e.g., in the form of injectable microspheres loaded with a local anesthetic in sustained release form, into a site at or adjacent to a nerve or nerves innervating a body region to provide local anesthesia. Thus, the safe local anesthetic formulation according to the invention can be injected, infiltrated or implanted at a site in a patient where the local anesthetic agent is to be released. Optionally, the safe local anesthetic formulation can also be applied topically, e.g., to skin and/or mucosal surfaces.

Further aspects of the invention are directed to a method of treating a patient in need of a surgical procedure, comprising placing a safe local anesthetic form in proximity to a nerve or nerves at the surgical site.

Therefore, the present invention provides for safe regional local anesthesia at a site in a patient, by administering at the site a local anesthetic incorporated in a biocompatible, biodegradable, controlled release formulation where the site of administration is located at or adjacent to a nerve or nerves innervating a region of the patient to be so anesthetized. Further, the local anesthetic is present in a concentration effective to safely achieve sensory or motor local anesthesia with reduced toxicity, and the local anesthetic is released at a rate effective to safely achieve sensory or motor local anesthesia. In one aspect, the method of the invention provides for at least a portion of the local anesthetic in immediate release form.

In one preferred embodiment, the method provides for preparing the controlled release form as a plurality of microspheres, suspending the microspheres in a pharmaceutically acceptable medium for injection, and injecting said microspheres at a site in a patient, for example, in proximity to a nerve to be anesthetized. The local anesthetic can be incorporated into the formulation, such as, for example the plurality of controlled release microspheres at a percent loading of 0.1% to 90% and in a preferred embodiment, at a percent loading ranging from about 20% to about 80%, by weigh, and in a more preferred embodiment, at a percent loading ranging from about 70% to about 80%, by weight.

Although any pharmaceutically acceptable local anesthetic may be employed according to the method of the invention, the local anesthetic is preferably selected from bupivacaine, dibucaine, procaine, chloroprocaine, prilocaine, mepivacaine, etidocaine, tetracaine, lidocaine and xylocaine, and salts, derivatives or mixtures thereof. In a more preferred embodiment, the local anesthetic is bupivacaine. The method can be conducted with bupivacaine HCl, bupivacaine free base and/or mixtures thereof While the artisan will understand that the dose will vary according to the size and weight of the patient and the number of nerves to be blocked and/or treated, the bupivacaine is administered in a dose ranging from 5 through 450 mg/kg of a patient. Alternatively, bupivacaine is administered according to the invention in a dose ranging from about 0.5 mg to about 200 mg or more, depending upon the aforementioned factors. Preferably, bupivacaine is administered in a dose ranging from about 1 to about 50 mg or more, and more preferably, bupivacaine is administered in a dose ranging from about 1 to about 20 mg, depending upon the above listed factors. Of course, the artisan will appreciate that the dosage ranges of other art-known local anesthetics can be determined relative to the potency of bupivacaine.

The method of the invention may also be conducted by administering a formulation prepared as a unit dosage of the controlled release formulation comprising, in a container, a sufficient amount of the formulation to induce local anesthesia in at least one patient. In one embodiment, the unit dosages are sterile and lyophilized. Alternatively, the unit dosages are sterile and prepared as a suspension in a solution acceptable for injection into a patient.

The controlled release local anesthetic dosage form may be injected and/or infiltrated, at the site where the anesthetic is to be released. This can be prior to surgery, at the time of surgery, or following removal (discontinuation) or reversal of a systemic anesthetic.

According to the invention, an effective local anesthetic dose of the biocompatible, biodegradable, controlled release formulation according to the invention will, when injected into the patient intravenously, fail to induce a toxic reaction or alternatively, be much less likely to induce a toxic reaction relative to the toxicity of bupivacaine HCl or bupivacaine free base. In another aspect, when the local anesthetic is bupivacaine an intravenously administered dose, measured by the amount required to produce an effective local anesthesia, of the biocompatible, biodegradable, controlled release formulation will be unable to produce a bupivacaine blood plasma level of about 1600 ng/ml or, alternatively, no more than about 1200 ng/ml of plasma bupivacaine. In a further aspect, when the local anesthetic is bupivacaine, an intravenously administered dose, measured by the amount required to produce an effective local anesthesia, of the biocompatible, biodegradable, controlled release formulation will be unable to produce a bupivacaine blood plasma higher than from about 200 to about 650 ng/ml.

Examples demonstrate the greatly enhanced safety and greatly reduced toxicity provided by the methods and formulations according to the invention.

BRIEF DESCRIPTION OF THE DRAWINGS

The following drawings are illustrative of embodiments of the invention and are not meant to limit the scope of the invention as encompassed by the claims.

DETAILED DESCRIPTION

Accordingly, methods and formulations according to the invention unexpectedly provide substantially safer methods and formulation for inducing local anesthesia at a desired site in a patient (human or animal). Applicants have discovered that controlled release formulations according to the invention surprisingly provide essentially normal, not delayed, onset of local anesthesia where administered, but does avoid the release of sufficient incorporated local anesthetic in toxic amounts, even when, e.g., 10 times an otherwise lethal amount of the anesthetic is administered.

Thus, methods for providing local anesthesia having greatly enhanced safety are provided which are achieved by the administration of formulations for the safe and regulated delivery of a local anesthetic agent to a targeted area. These methods can be used for the safe management of various forms of acute pain, such as dental pain, or for persistent pain, such as postoperative pain, sympathetically maintained pain, or certain forms of chronic pain such as the pain associated with many types of cancer. These systems may also be used for blockade of nociceptive pathways (afferent and efferent) in patients with acute pancreatitis, ileus, or other visceral disorders, As used herein, the term "local anesthetic agent" means any drug which provides local numbness and/or analgesia. Examples of local anesthetic agents which can be used include bupivacaine, ropivacaine, dibucaine, procaine, chloroprocaine, prilocaine, mepivacaine, etidocaine, tetracaine, lidocaine, and xylocaine, and mixtures thereof The local anesthetic can be in the form of a salt, for example, the hydrochloride, bromide, acetate, citrate, carbonate or sulfate. More preferably, the local anesthetic agent is in the form of a free base. The free base provides a slower initial release and avoids an early "dumping" of the local anesthetic at the injection site. Preferred local anesthetic agents include, e.g., bupivacaine. Bupivacaine is a particularly long acting and potent local anesthetic agent when incorporated into a PLAM or other controlled release formulation. Its other advantages include sufficient sensory anesthesia without significant motor blockade, lower toxicity, and wide availability. Anesthetics typically administered systematically may also be used in those cases where the means of administration results only in a local effect, rather than systemic.

The term "local anesthetic" may also encompass, pursuant to the definitions provided herein, a drug of a different class than those traditionally associated with local anesthetic properties, including but not limited to morphine, fentanyl, and agents which, for example, can provide regional blockade of nociceptive pathways (afferent and/or efferent).

The terms "safe" or "safety" as used herein describes a substantial reduction in the risk of a toxic reaction or effect resulting from administration of a local anesthetic by the methods of the present invention compared to the risk of a toxic reaction or effect resulting from the administration of a local anesthetic agent administered by a method not using a local anesthetic incorporated into a controlled release formulation for regulated release at the site of action.

For example, toxicity to bupivacaine is associated with plasma concentrations in excess of 1600 ng/ml. When controlled release bupivacaine is administered according to the methods of the invention, even at doses 10-fold higher than those required to achieve prolonged anesthesia, plasma bupivacaine doses not exceed 200 to 650 ng/ml.

As used herein, the term "patient" broadly refers to any animal that is to be treated with the compositions and by the methods herein disclosed. The methods of the invention using the disclosed local anesthetic dosage forms can provide localized pain blockade to any animal, e.g., any vertebrate, which it is desired to so anesthetize. In particular, the disclosed methods and compositions will find use in veterinary practice and animal husbandry for, e.g., birds and mammals, wherever prolonged local anesthesia is convenient or desirable. In a preferred embodiment, the term "patient" includes humans in need of or desiring local anesthesia of greatly enhanced safety.

Any pharmaceutically acceptable formulation suitable for local implantation, infiltration or injection in proximity to a nerve that is able to provide a safe and controlled release of an effective amount of a local anesthetic agent and/or a glucocorticoid may be employed to provide for safe local anesthesia as needed. Art known slow release formulations and/or carriers, e.g., emulsions, liposomes, gels, suspensions, biocompatible polymers and gum matrices may be employed. Slow release formulations according to the invention also include, e.g., specially coated pellets, polymer formulations or matrices for surgical insertion or controlled release microparticles or microspheres for implantation, insertion or injection, wherein the slow release of the active medicament is brought about through controlled diffusion out of the formulation and/or selective breakdown of the coating of the preparation, or selective breakdown of a polymer matrix, if present.

The safety enhancing methods according to the invention may be provided in conjunction with any implantable, insertable or injectable system known in the art, including but not limited to microspheres, microcapsules, gels, pastes, implantable rods, pellets, plates or fibers, and the like (generically referred to as "substrates").

In a preferred embodiment, the slow release formulation is prepared as microspheres in a size distribution range suitable for local injection. The diameter and shape of the microspheres or other particles can be manipulated to modify the release characteristics. For example, larger diameter microspheres will typically provide slower rates of release and reduced tissue penetration and smaller diameters of microspheres will produce the opposite effects, relative to microspheres of different mean diameter but of the same composition. In addition, other particle shapes, such as, for example, cylindrical shapes, can also modify release rates by virtue of the increased ratio of surface area to mass inherent to such alternative geometrical shapes, relative to a spherical shape. The diameter of injectable microspheres are in a size range, for example, from about 5 microns to about 200 microns in diameter. In a more preferred embodiment, the microspheres range in diameter from about 20 to about 120 microns.

A wide variety of biodegradable materials may be utilized to provide the controlled release of the local anesthetic. Any pharmaceutically acceptable biodegradable polymers known to those skilled in the art may be utilized.

The controlled release material should be biocompatible and be degraded, dissolved or absorbed in situ in a safe and pharmaceutically acceptable manner so that the material is removed from the injection or implantation site by natural tissue processes and in a suitable amount of time, e.g., less than one year, preferably less than 6 months, and most preferably in less than one month. In any event, the carrier may be removed by local tissue processes without causing untoward local tissue reaction, or systemic or local toxicity. In the case of polymeric materials, biocompatibility is enhanced by preparing the polymeric materials in a pharmaceutically acceptable manner, i.e., employing purification techniques well known to the art, e.g., recrystallization of either the monomers forming the polymer and/or the polymer and other techniques for producing materials for implantation or injection into living tissue.

Suitable biodegradable polymers can be utilized as the controlled release material. The polymeric material may comprise a polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like. Preferred controlled release materials which are useful in the formulations of the invention include the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other useful polymers include protein polymers such as gelatin and fibrin and polysaccharides such as hyaluronic acid. Since polylactic acid takes at least one year to degrade in vivo, this polymer should be utilized by itself only in circumstances where such a degradation rate is desirable or acceptable.

Commercially available polymers include, for example, poly(d,l-lactic-co-glycolic acid) and preferably 50:50 poly (D,L) lactic co-glycolic acid having a mole percent composition of 50% lactide and 50% glycolide. Other suitable commercially available products include 65:35 DL, 75:25 DL, 85:15 DL and poly(d,l-lactic acid) (d,l-PLA). Poly (lactide-co-glycolides) are commercially available, for example, from Boerhinger Ingelheim (Germany) under its Resomer© mark, e.g., PLGA 50:50 (Resomer RG 502), PLGA 75:25 (Resomer RG 752) and d,l-PLA (resomer RG 206), and from Birmingham Polymers (Birmingham, Ala.). These copolymers are available in a wide range of molecular weights and ratios of lactic to glycolic acid.

Proteinaceous polymers, may also be used. Proteinaceous polymers and their soluble derivatives include gelation biodegradable synthetic polypeptides, elastin, alkylated collagen, to alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alamine, L-lysine, L-phenylalanine, L-valine, L-tyrosine, and the like.

In embodiments where the biodegradable polymer comprises a gel, one such useful polymer is a thermally gelling polymer, e.g., polyethylene oxide, polypropylene oxide (PEO-PPO) block copolymer such as Pluronic® F127 from BASF Wyandotte. In such cases, the local anesthetic formulation may be injected via syringe as a free-flowing liquid, which gels rapidly above 30° C. (e.g., when injected into a patient). The gel system then releases a steady dose of local anesthetic at the site of administration.

In additional embodiments of the invention, the controlled release material, which in effect acts as a carrier for the local anesthetic, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan. Further, the pharmacokinetic release profile of these formulations may be first order, zero order, bi- or multi-phasic, to provide the desired reversible local anesthetic effect over the desired time period.

Definitions or further descriptions of any of the foregoing terminology are well known in the art and may be found by referring to any standard biochemistry reference text such as "Biochemistry" by Albert L. Lehninger, Worth Publishers, Inc. and "Biochemistry" by Lubert Stryer, W.H. Freeman and Company, both of which are hereby incorporated by reference.

The aforementioned biodegradable hydrophobic and hydrophilic polymers are particularly suited for the methods and compositions of the present invention by reason of their characteristically low human toxicity and virtually complete biodegradability.

A desired release profile can be achieved by using a mixture of polymers having different release rates and/or different percent loading of local anesthetic and/or augmenting agent, for example, polymers releasing in one day, three days, and one week, so that linear release is achieved even when each polymer per se does not release linearly over the same time period. In addition, a mixture of microspheres having one or more different local anesthetic agents, having the same or different controlled release profile, can be utilized to provide the benefits of different potencies and spectrum of activity during the course of treatment.

Methods for manufacture of microspheres are well known and are typified in the following examples. Examples of suitable methods of making microspheres include solvent evaporation, phase separation and fluidized bed coating.

In solvent evaporation procedures, the local anesthetic agent, if soluble in organic solvents, may be entrapped in the biodegradable polymer by dissolving the polymer in a volatile organic solvent, adding the drug to the organic phase, emulsifying the organic phase in water which contains less than 2% polyvinyl alcohol, and finally removing the solvent under vacuum to form discrete, hardened monolithic microspheres.

Phase separation microencapsulation procedures are suitable for entrapping water-soluble agents in the polymer to prepare microcapsules and microspheres. Phase separation involves coacervation of the polymer from an organic solvent by addition of a nonsolvent such as silicone oil.

In fluidized bed coating, the drug is dissolved in an organic solvent along with the polymer. The solution is then processed, e.g., through a Wurster air suspension coater apparatus to form the final microcapsule product.

The biodegradable controlled release materials may be used in order to prepare controlled release local anesthetic implants. The implants may be manufactured, e.g., by compression molding, injection molding, and screw extrusion, whereby the local anesthetic agent is loaded into the polymer. Implantable fibers can be manufactured, e.g., by blending the local anesthetic agent with the controlled release material and then extruding the mixture, e.g., under pressure, to thereby obtain biodegradable fibers.

In other embodiments of the invention, the controlled release material comprises an artificial lipid vesicle, or liposome. Liposomes are well known in the art as carriers of bioactive or pharmacologically active substances such as drugs. Liposomes as described herein will vary in size. Preferably, the liposomes have a diameter between 100 nm and 10 microns or greater. A wide variety of lipid materials may be used to form the liposomes including natural lecithins, e.g., those derived from egg and soya bean, and synthetic lecithins, the proviso being that it is preferred that the lipids are non-immunogenic and biodegradable. Also, lipid-based materials formed in combination with polymers may be used, such as those described in U.S. Pat. No. 5,188,837 to Domb, (incorporated by reference herein).

Examples of synthetic lecithins which may be used together with their respective phase transition temperatures, are di-(tetradecanoyl)phosphatidylcholine (DTPC) (23 C), di-(hexadecanoyl)phosphatidylcholine (DHPC) (41 C) and di-(octandecanoyl) phosphatidylcholine (DOPC) (55 C). Di-(hexadecanoyl) phosphatidycholine is preferred as the sole or major lecithin, optionally together with a minor proportion of the di-(octadecanoyl) or the di-(tetradecanoyl) compound. Other synthetic lecithins which may be used are unsaturated synthetic lecithins, for example, di-(oleyl) phosphatidyl-choline and di-(linoleyl)phosphatidylcholine. In addition to the main liposome-forming lipid or lipids, which are usually phospholipids, other lipids (e.g. in a proportion of 5–40% w/w of the total lipids) may be included, for example, cholesterol or cholesterol stearate, to modify the structure of the liposome membrane, rendering it more fluid or more rigid depending on the nature of the main liposome-forming lipid or lipids.

In other preferred formulations, the lipids containing the local anesthetic agent are dispersed in a pharmaceutically acceptable aqueous medium. In a further embodiment, a portion of the dose of the local anesthetic is incorporated into the aqueous medium in immediate release form to form an aqueous pharmaceutical suspension useful for administration at the desired site in the patient to be anesthetized. This may be accomplished via injection or implantation. Liposomes may be prepared by dissolving an appropriate amount of a phospholipid or mixture or phospholipids together with any other desired lipid soluble components (e.g., cholesterol, cholesterol stearate) flowing in a suitable solvent (e.g., ethanol) and evaporating to dryness. An aqueous solution of the local anesthetic, optionally with augmenting agent, may then be added and mixed until a lipid film is dispersed. The resulting suspension will contain liposomes ranging in size, which may then fractionated to remove undesirable sizes, if necessary. This fractionation may be effected by column gel chromatography, centrifugation, ultracentrifugation or by dialysis, as well known in the art.

The above method of preparation of liposomes is representative of a possible procedure only. Those skilled in the art will appreciate that there are many different methods of preparing liposomes, all of which are deemed to be encompassed by the present disclosure.

In certain embodiments where the substrate is a microsphere, the microspheres include from about 5% to about 95% drug and from about 5% to about 95% polymer, by weight. In certain preferred embodiments, the drug is included in the microspheres in an amount from about 20% to about 90%, more preferably from about 60% to about 80%, and more preferably from about 70 to about 75%, by weight (high-microspheres).

The term "microspheres" are defined for purposes of the present invention as particles comprising local anesthetic and e.g., the aforementioned polymeric materials (used as a controlled release carrier for the drug) which are preferably anywhere from about 20 microns to about 200 microns, and more preferably from about 45 to about 90 microns in diameter. The microspheres are preferably formed in such a size as to be injectable. For purposes of the present invention, the term "microsphere" encompasses "microparticle" and "microcapsule". The polymeric material used in the microspheres of the present invention preferably have a molecular weight from about 5,000 to about 200,000.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539 (Ludwig, et al.), hereby incorporated by reference. Basically, therein the copolymers are prepared by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is form about 0.01 to about parts by weight relative to the total weight of combined lactic acid and glycolic acid. The polymerization reaction may be conducted without solvents at a temperature from about 100 C. to about 250 C. for about 48 to about 96 hours, preferably under a reduced pressure to facilitate removal of water and by-products. The copolymer is then recovered by filtering the molten reaction mixture to remove substantially all of the catalyst, or by cooling and then dissolving the reaction mixture in an organic solvent such as dichloromethane or acetone and then filtering to remove the catalyst.

Polyanhydrides may be prepared in accordance with the methods set forth in U.S. Pat. No. 4,757,128, hereby incorporated by reference. For example, polyanhydrides may be synthesized by melt polycondensation of highly pure dicarboxylic acid monomers converted to the mixed anhydride by reflux in acetic anhydride, isolation and purification of the isolated prepolymers by recrystallization, and melt polymerization under low pressure ($10^{-4}$ mm) with a dry ice/acetone trap at a temperature between 140–250 C. for 10–300 minutes. High molecular weight polyanhydrides are obtained by inclusion of a catalyst which increases the rate of anhydride interchain exchange, for example, alkaline earth metal oxides such as CaO, BaO and $CaCO_3$. Polyorthoester polymers may be prepared, e.g., as set forth in U.S. Pat. No. 4,070,347, hereby incorporated by reference.

Various commercially available poly (lactide-co-glycolide) materials (PLGA) may be used in the preparation of the microspheres of the present invention. For example, poly(d,l-lactic-co-glycolic acid) are commercially available. A preferred commercially available product is a 50:50 poly (D,L) lactic co-glycolic acid having a mole percent composition of 50% lactide and 50% glycolide. Other suitable commercially available products are 65:35 DL, 75:25 DL, 85:15 DL and poly(d,l-lactic acid) (d,l-PLA). For example, poly(lactide-co-glycolides) are also commercially available from Boerhinger Ingelheim (Germany) under its Resomer© mark, e.g., PLGA,50:50 (Resomer RG 502), PLGA75:25 (Resomer RG 752) and d,l-PLA (resomer RG 206), and from Birmingham Polymers (Birmingham, Ala.). These copolymers are available in a wide range of molecular weights and ratios of lactic to glycolic acid.

The polymers utilized in the microspheres of the present invention may be prepared, e.g., by the condensation of lactic acid and glycolic acid in the presence of a readily removable polymerization catalyst. Such catalysts include strong acid ion-exchange resins in the form of beads or similarly hard structures which are easily removed by filtration or similar techniques. Further information concerning the preparation of the copolymers of the present invention is readily available to those skilled in the art, and may be ascertained from, e.g., U.S. Pat. No. 4,293,539 (Ludwig, et al.), hereby incorporated by reference.

Pharmaceutically acceptable polyanhydrides which are useful in the present invention have a water-labile anhydride linkage. The rate of drug release can be controlled by the particular polyanhydride polymer utilized and its molecular weight. The polyanhydride polymer may be branched or linear. Examples of polyanhydrides which are useful in the present invention include homopolymers and copolymers of poly(lactic acid) and/or poly(glycolic acid), poly[bis(p-carboxyphenoxy)propane anhydride] (PCPP), poly[bis(p-carboxy)methane anhydride] (PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids.

The biodegradable controlled release microspheres of the present invention may be prepared by any procedure known to those skilled in the art. In certain preferred embodiments, however, the microspheres may be obtained by utilizing a solvent extraction technique (reactor process) which involves dissolving the drug and the polymer in an organic solvent such as ethyl acetate. This solution thereby obtained (the dispersed phase) is added to a solution of, e.g., polyvinyl alcohol (PVA) in water (the continuous phase) with stirring. The emulsion thereby formed is then added to water in order to extract the solvent and to harden the microspheres. The mixture is then filtered and the microspheres are dried. One appropriate method of drying is, e.g., under vacuum at room temperature. The desired particle size fraction is then collected by sieving. The organic solvent utilized is preferably ethyl acetate; however, any pharmaceutically acceptable organic solvent may be utilized, such as acetone, ethanol, diethyl ether, methanol, benzyl alcohol, methylene chloride, petroleum ether or others. This procedure is particularly useful for preparing microspheres of bupivacaine base.

Alternatively, the microspheres of bupivacaine base may be prepared by dissolving the drug and polymer in ethyl acetate and thereafter spray drying the solution.

In instances where the microspheres are to incorporate drugs which are very water soluble and insoluble in ethyl acetate, such as bupivacaine HCl, the microspheres may be prepared using a coacervation/phase separation rather than the solvent extraction technique described above. However, the solvent extraction technique can be used with bupivacaine HCl due to its low water solubility at pH 7.4 and above. The coacervation/phase separation technique utilized involves dissolving the polymer in ethyl acetate and suspending micronized bupivacaine HCl in the solution. Silicone oil is then added to form the microspheres. This mixture is then added to heptane to harden the microspheres, which are then separated by filtration. The microspheres are dried under a vacuum at room temperature. The desired particle size fraction is then collected by sieving.

Alternatively, microspheres prepared using bupivacaine HCl may be accomplished by suspending the drug in a solution of polymer in ethyl acetate or in methylene chloride and methanol and spray drying.

Alternatively, the bupivacaine HCl may be dissolved in water, and the polymer may be dissolved in ethyl acetate. The water phase then can be added to the organic phase and homogenized to yield a W/O emulsion. The drug being in the water phase would then be surrounded by polymer (oil phase). This is then added to the PVA solution in water with stirring to form a W/O emulsion. The solvent would diffuse out, leaving microspheres. Additional cold water can be added to harden the microspheres. This process may yield more uniform microspheres without requiring micronization of the drug. Also, as the drug will be surrounded by polymer, the release of the drug may be more uniform and would be diffusion-controlled.

The ultimate drug content of the microspheres according to the present invention may be varied substantially, depending upon whether a high load or a low load formulation procedure is utilized. In certain preferred embodiments (e.g., where the drug is bupivacaine), the drug content of the high-load microspheres may be from about 40 to about 95%, preferably from about and more preferably from about 70% to about 75% of the total weight of the microsphere, and the drug content of the low-load microspheres may be from about 0.1 to about 40% and from about 5% to about 40%.

In one preferred embodiment of the present invention, the drug included in the microspheres is a local anesthetic either of the ester or amide type. Suitable local anesthetics of the ester type include the benzoic acid esters (e.g., piperocaine, meprylcaine, isobucaine), the para-aminobenzoic acid esters (e.g., procaine, tetracaine, butethamine, propoxycaine, chloroprocaine); meta-aminobenzoic acid esters (e.g., metabutetharine, primacaine), paraethoxy-benzoic acid esters (e.g., parethoxycaine), and their pharmaceutically acceptable salts. The non-esters include, e.g., lidocaine, mepivacaine, pyrrocaine, prilocaine, bupivacaine, etidocaine, pharmaceutically acceptable salts. A most preferred local anesthetic is bupivacaine.

In certain preferred embodiments of the present invention, the microspheres incorporate bupivacaine as the drug in an amount from about 45% to about 70% by weight, the copolymer being PLGA 50:50 of a molecular weight from about 5,000 to about 200,000.

The microspheres of the present invention preferably provide a sustained action in the localized area to be treated. For example, when the drug included in the microspheres is bupivacaine, it would be desirable that such a formulation could provide localized anesthesia to the area in question for a period of one day, two days, three days, or longer. The formulations can therefore, of course, be modified in order to obtain such a desired result.

The microspheres of the present invention may be utilized as a controlled release formulation preferably by incorporating an effective amount of the same into a pharmaceutically acceptable solution (e.g., water) or suspension for injection. The final reconstituted product viscosity may be in a range suitable for the route of administration. In certain instances, the final reconstituted product viscosity may be, e.g., about 35 cps. Administration may be via the subcutaneous or intramuscular route. However, alternative routes are also contemplated, and the formulations may be applied to the localized site in any manner known to those skilled in the art, such that a localized effect is obtained. The microspheric formulations of the present invention can be implanted at the site to be treated. Thereby, the formulations of the present invention, when including a local anesthetic, may be used in the control of post-operative pain.

The dosage of the controlled release microsphere formulations of the present invention is dependent upon the kind and amount of the drug to be administered, the recipient animal, and the objectives of the treatment. For example, when the drug included in the microspheres of the present invention is bupivacaine, the formulation may include, e.g., from about 0.5 to about 2 mg/kg body weight. The effective dose of bupivacaine, or an amount of another local anesthetic sufficient to provide proportional potency can range from about 1 to 50 mg of bupivacaine injected or inserted at each site where the release of a local anesthetic agent is desired. In certain preferred embodiments, the dose of bupivacaine in the controlled release dosage form of the invention is sufficient to provide a controlled release of about 1 to 4 mg per day at the release site for at least 1 to 4 days. Since the formulations of the present invention are controlled release, it is contemplated that formulations may include much more than usual immediate release doses, e.g., as much as 120 mg/kg bupivacaine or more.

The local anesthetic is incorporated into the polymer or other controlled-release formulation in a percent loading between 0.1% and 90%, by weight, preferably between 5% and 75%, by weight. It is possible to tailor a system to deliver a specified loading and subsequent maintenance dose by manipulating the percent drug incorporated in the polymer and the shape of the, matrix or formulation, in addition to the form of local anesthetic (e.g., free base versus salt) and the method of production. The amount of drug released per day increases proportionately with the percentage of drug incorporated into the formulation, e.g., matrix (for example, from 5 to 10 to 20%). In the preferred embodiment, polymer matrices or other formulations drug incorporated from about 70% to about 75% by weight, are utilized, although it is possible to incorporate substantially more drug, depending on the drug, the method used for making and loading the device, and the polymer.

The rate of release of local anesthetic agent or other drugs incorporated into the formulation will also depend on the solubility properties of the local anesthetic or drug. The greater the solubility in water, the more rapid the rate of release in tissue, all other parameters being unchanged. For example, those local anesthetic agents having pH dependent solubility will be released more rapidly at the optimum pH for those compounds. Thus, the formulation may be optimized for the desired local anesthetic, release rate, by selecting local anesthetic agents having a desired water solubility in tissue, e.g., at tissue pH. Thus, a local anesthetic agent that is more soluble at acid pH will have a faster release rate in a relatively acidic (e.g., pH less than about 7.2) tissue. For example, in one embodiment, the formulation will have released, in vitro, at least 70 percent of a local anesthetic at 48 hours at about pH 6 and will have released at least 40 percent of a local anesthetic at a pH ranging from about 7.4 to about 8, at 48 hours. Other combinations are pH independent in their release.

Potential applications include any condition for which safe localized anesthesia is desirable. This includes both nerve blockade for the relief of pain and motor symptoms as well as nerve blockade for other medical purposes. The methods according to the invention can be used to provide safe local anesthesia such as, for example, two to five day intercostal blockade for thoracotomy, or longer term intercostal blockade for thoracic post-therapeutic neuralgia, lumbar sympathetic blockade for reflex sympathetic dystrophy, or three-day ilioinguinal/iliohypogastric blockade for hernia repair. Other potential applications include local anesthesia having enhanced safety for obstetrical or gynecological procedures. Yet further potential applications include providing localized temporary sympathectomy, e.g., blockade of sympathetic or parasympathetic ganglia to treat a variety of autonomic diseases, including circulatory dysfunction or cardiac dysrhythmias with enhanced safety. The formulations may also be used to treat trigeminal neuralgia and other diseases of the cranial nerves as well as to provide temporary nerve blockade to treat localized muscle spasm and treatment of retrobulbar conditions, e.g., eye pain. Other uses include intra-operative administration in order to reduce pain during and after the operative procedure, especially for plastic surgery procedures where prolonged nerve blockade will enhance the outcome having enhanced safety. These are merely examples, and additional uses for both human and veterinary practice are immediately apparent to the artisan.

Methods of Administration

In a preferred method of administration a dosage form, e.g., microspheres, are administered by injection into a site where local anesthetic agent is to be released. Microspheres may be injected through a syringe or a trochar. Pellets or slabs may be surgically placed into a site where release of oral anesthetic agent is desired.

The microspheres may be prepared from PLGA polymers ranging from, for example, PLGA in a ratio of 50:50, 65:35 or 75:25. An optimum composition has been determined to be PLGA 65:35. The microspheres, formulated with, e.g., PLGA 65:35 microspheres are administered in a dose ranging from, for example, 2 through 450 mg of microspheres 75% (w/w) loaded with a local anesthetic such as bupivacaine, per kg of the patient to be treated. In a preferred embodiment the dose ranges from 50 through 450 m/kg. In a more preferred embodiment the dose ranges from about 10 to about 150 mg/kg with PLGA 65:35. Certainly, the artisan will appreciate the fact that the dose ranges mentioned above are based on the potency of bupivacaine, and that exact effective dosages will vary with the particular relative potency and pharmacokinetic of each local anesthetic and will be able to readily adjust the dose according to the degree of blockade experienced by the patient.

The formulation described herein can also be used to administer local anesthetic agents that produce modality-specific blockade, as reported by Schneider, et al., *Anesthesiology*, 74:270–281 (1991), or that possess physical-chemical attributes that make them more useful for sustained release then for single injection blockade, as reported by Masters, et al., *Soc. Neurosci. Abstr.*, 18:200 (1992), the teachings of which are incorporated herein.

Safety Enhancement

It has been found that the methods according to the invention utilizing safe, regulated release local anesthetic preparations provides at least an order of magnitude reduction in the risk of toxic and/or untoward effects relative to conventional methods for providing local anesthesia.

Studies were conducted with a microsphere preparation composed of poly (lactide-co-glycolide) materials (PLGA) in the ratio of 65:35 with a size range of 25–125 m, loaded with from about 70% to about 75% (w/w) with the local anesthetic bupivacaine (referred to hereinafter as long acting bupivacaine or "LAB"). Doses of drug refer to bupivacaine dose; thus, total mass administered is 1.33 times the indicated dose of LAB. Methods for inducing local anesthesia with these materials have been evaluated in test animals; including rats, dogs and sheep.

Dose-duration studies in these species; with administration of bupivacaine, indicates that duration of local anesthesia is a function of the amount of bupivacaine injected around a nerve, rather than the amount injected per unit of body weight. It has been determined that the optimal dose of bupivacaine ranges from about 1 to about 100 mg per nerve and more preferrably from about 25 to about 75 mg per nerve or about 40 to 50 mg per nerve and most preferrably at about 50 mg per nerve. Measurements conducted on both sensory and motor nerve blockade provided similar results.

In tests with formulations according to the present invention, using long acting bupivacaine ("LAB") formulations, the data indicates that even at doses 10-fold higher than those required to achieve three to five days of anesthesia, plasma bupivacaine doses not exceed 200 to 650 ng/ml. This results in an exceptional safety margin since toxicity to bupivacaine is associated with plasma concentrations in excess of 1600 ng/ml. In rats, local injection of 25 mg/kg (8 mg/nerve) of commercial aqueous bupivacaine HCl results in the deaths of about 10% of the animals. Using the LAB preparation, 150 mg/kg (50 mg/nerve) resulted in three to five days of local anesthesia and even 600 mg/kg (200 mg/nerve) resulted in only transient reduced activity in the rats. In dogs, subcutaneous doses of 300 mg/kg resulted in plasma bupivacaine concentrations in the range of 400 to 650 ng/ml for several days, without signs of toxicity. Further, simulated accidental direct injection of LAB intravenously resulted in no overt toxicity or microscopic pathology; even at extraordinarily high doses. This observation confirms. that LAB can provide both a prolonged duration of local anesthesia, as required, but a vastly improved therapeutic index for bupivacaine compared to conventional bupivacaine preparations, e.g., bupivacaine HLC.

EXAMPLES

Examples 1–3 (Solvent Extraction Process)

In Examples 1–3, bupivacaine microspheres are prepared by dissolving the bupivacaine base and the polymer in ethyl acetate. The polymer is 50:50 poly (D,L) lactic co-glycolic acid which has a mole percent composition of 50% lactide and 50% glycolide. This dispersed phase is then added to a solution of polyvinyl alcohol (PVA) in water (the continuous phase) with stirring. The resulting emulsion is monitored for droplet size, which is in turn controlled by the rate of stirring. The emulsion is then added to water to extract the solvent and to harden the microspheres. The mixture is then filtered and the microspheres are dried under vacuum at room temperature. The desired particle size fraction is then collected by sieving.

Each of Examples 1–3 are prepared such that the microspheres have a relatively high drug content. In Example 1, the theoretical drug content is about 60%, and the size of the microspheres range from about 45 to about 90 microns. In Example 2, the theoretical drug content is about 61%, and the range in the size of the microspheres is from about 45 to about 63 microns. In Example 3, the theoretical drug content is about 65%, and the range in particle size of the microspheres is from about 45 to about 63 microns.

The microspheres of Examples 1–3 are then suspended in a suitable media for injection, in this case water. Thereafter, the microspheres are subjected to in-vitro dissolution testing. An automated dissolution test method is utilized using the USP/NF Paddle Method II. The dissolution medium is 900 ml of Tris buffer with 0.05% sodium dodecyl sulfate at pH 7.4 at 37 C. with a stirring speed of about 50 RPM. The surfactant is added in order to prevent the microspheres from floating on the surface of the dissolution medium. The dissolution data for the microspheres of Examples 1–3 are presented in FIG. 1, and further information concerning these formulations is presented in Table 1 below.

TABLE 1

| Formulation | Microsphere Size | Theoretical % Drug | Actual % Drug | 50:50 dl-PLGA Polymer-MW | In vitro 24 Hours | Release 72 Hours |
|---|---|---|---|---|---|---|
| Ex. 1 | 45–90 | 62% | 47% | — | 28% | 68% |
| Ex. 2 | 45–63 | 61% | 56% | 50K | 52% | 91% |
| Ex. 3 | 45–63 | 65% | 59% | 50K | 22% | 46% |

Figure 1:
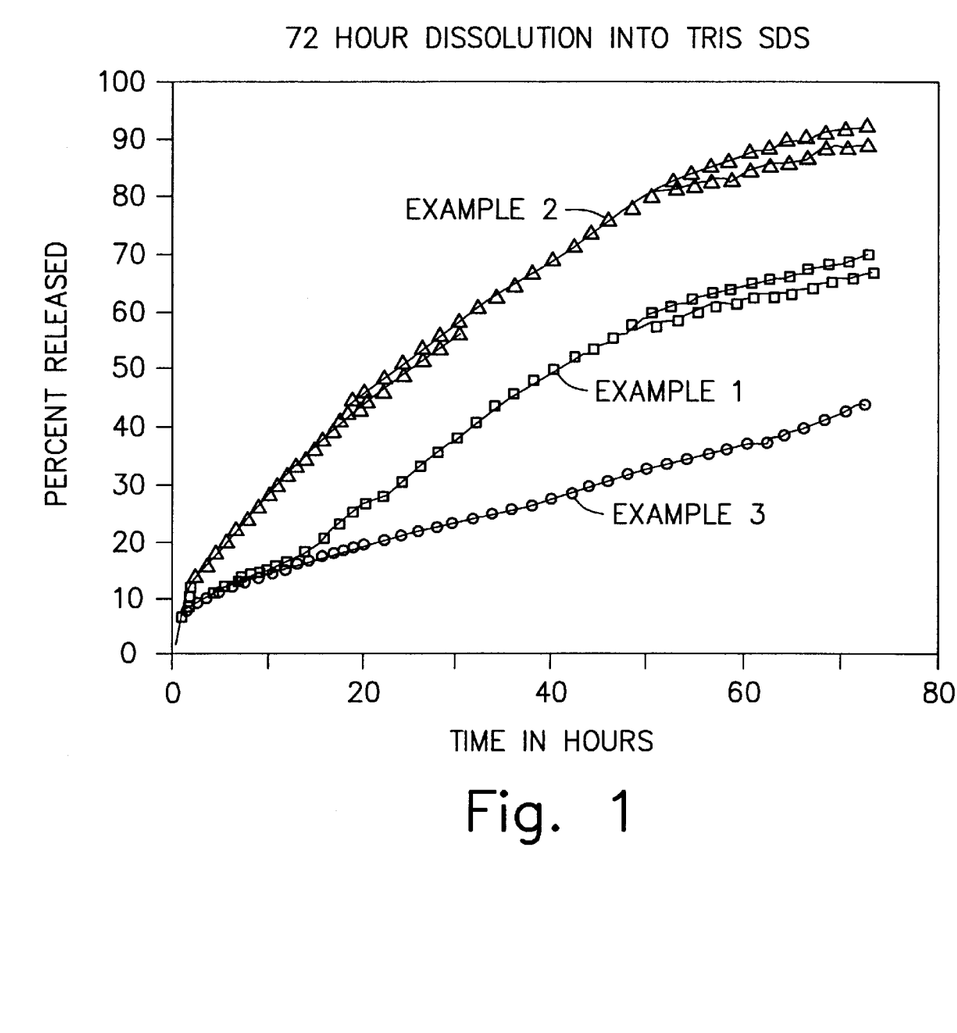
FIG. 1 is a graphical representation of the dissolution data obtained for Examples 1–3.

From the results set forth in FIG. 1 and Table 1, no correlation between drug content and release rate can be readily made.

It was expected that the formulation of Example 3 would release drug faster than that of Example 1 because of a higher drug content. However, the in-vitro release for Example 3 was slower than expected. It is hypothesized that this is due to the glass transition temperature of the polymer being lowered (below about 37 C.) by the high drug content. This situation may or may not be translated into in-vivo results.

Examples 4–9 (Spray-Dried)

In Examples 4–9, the bupivacaine base and the polymer utilized in Examples 1–3 are once again dissolved in ethyl acetate, but this time the microspheres are obtained by spray-drying the solution. Example 4 utilizes a relatively high drug content, whereas Example 5 utilizes a relatively low drug content. In Examples 7–9, microspheres having a substantially similar drug content to Examples 4–5 are prepared using the solvent extraction technique utilized in Examples 1–3. Details of the formulations are presented in Table 2 below.

TABLE 2

| Formulation | Drug Content (Theoretical) | Yield | Process |
|---|---|---|---|
| Ex. 4 | 49% | 55% | Spray-Dried |
| Ex. 5 | 29% | 64% | Spray-Dried |
| Ex. 6 | 45% | — | Spray-Dried |
| Ex. 7 | 47% | 62% | Solvent Extraction |
| Ex. 8 | 28% | 74% | Solvent Extraction |
| Ex. 9 | 60% | 60% | Solvent Extraction |

With regard to Example 9, the actual percentage of bupivacaine base in the microspheres is 51%, the molecular weight of the 50:50 dl-PLGA polymer is 18,000, the microspheres were about 45–63 microns, and in-vitro dissolution conducted as in Examples 1–3 showed that 61% of the bupivacaine was released in 22 hours.

Figure 2:
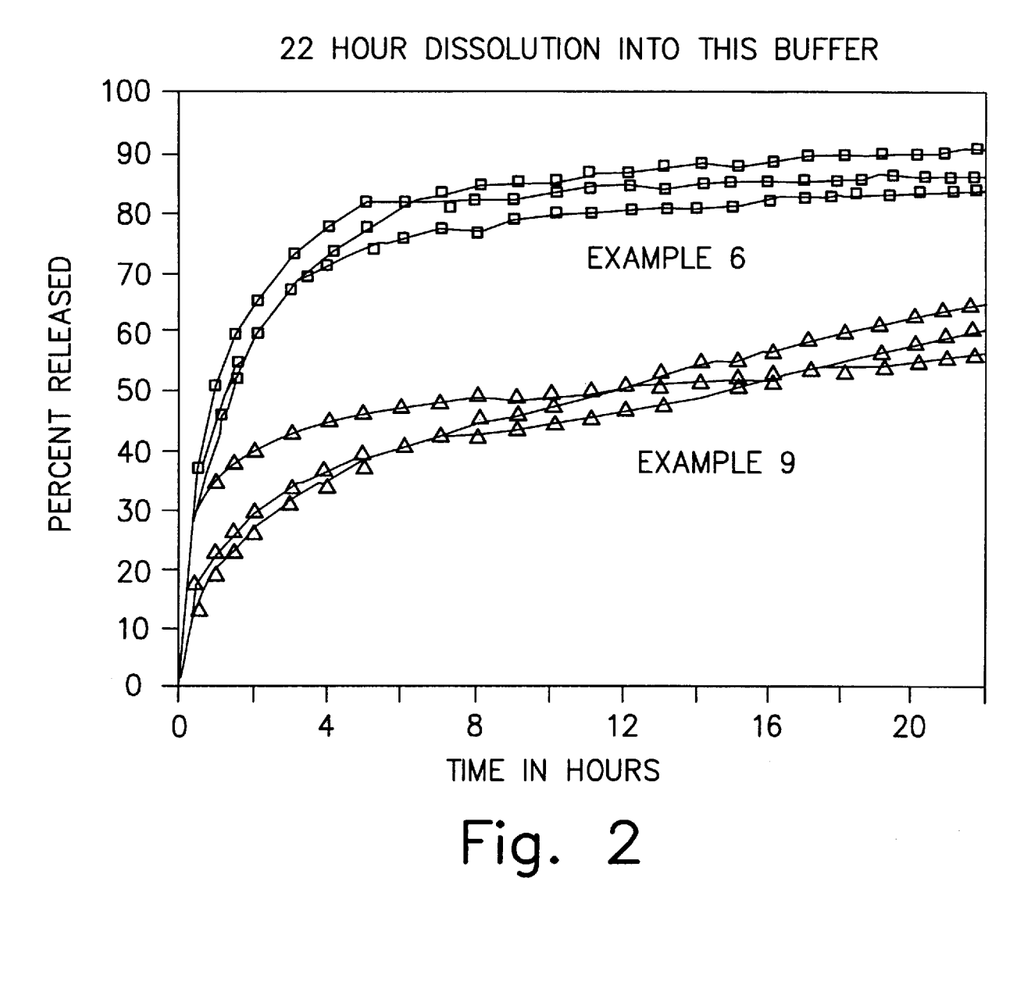
FIG. 2 is a graphical representation comparing the dissolution data obtained for Example 6 (spray-drying process) and Example 9 (solvent extraction process)

The microspheres of Examples 6 and 9 are suspended in a suitable injection medium (e.g., water) and then subjected to in-vitro dissolution testing via the procedures set forth in Examples 1–3. The in-vitro dissolution results are determined for 22 hours, and are graphically depicted in FIG. 2.

Figure 3:
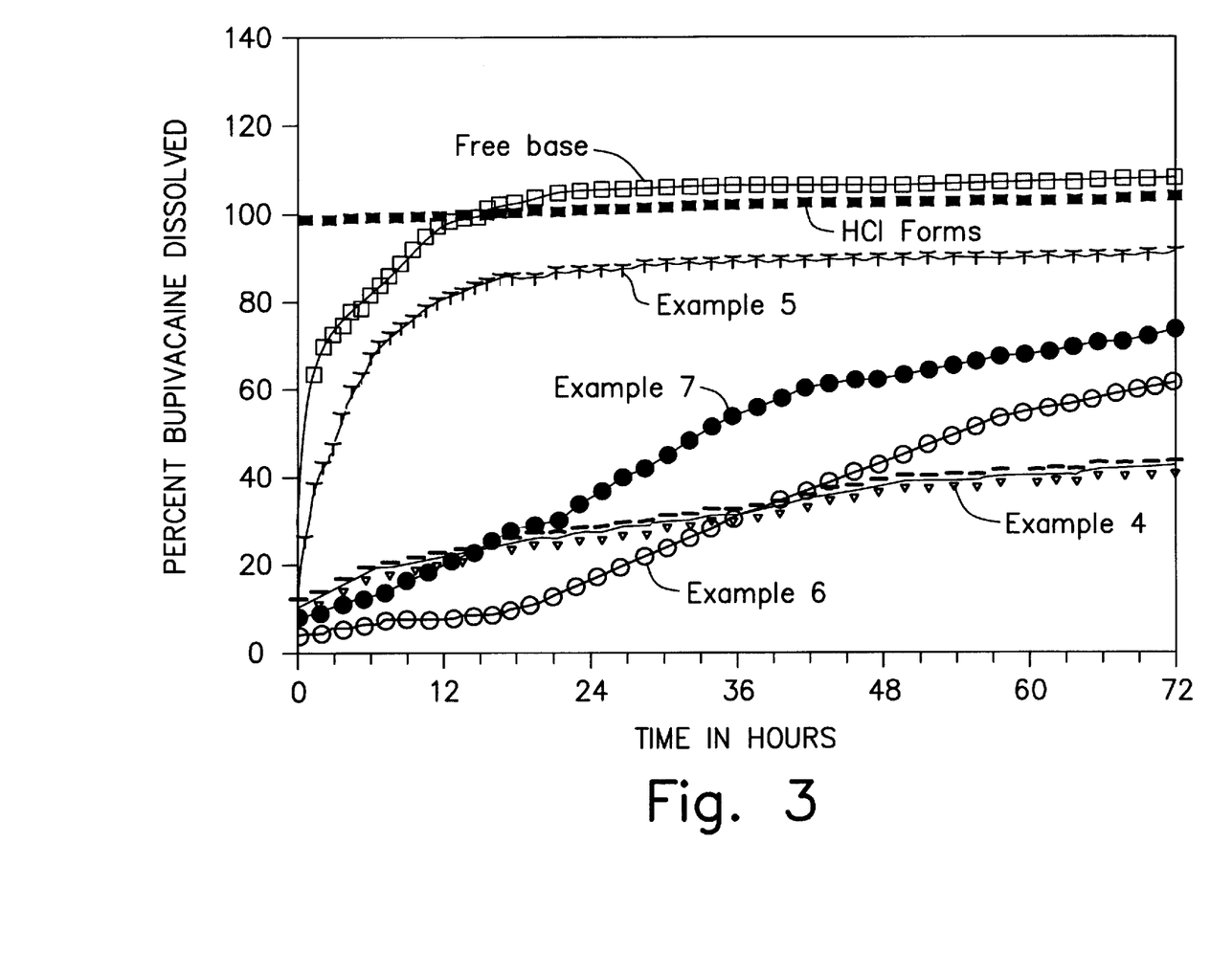
FIG. 3 is a graphical representation of the dissolution data obtained for Examples 4–5 (spray-drying process) and Examples 7–8 (solvent extraction process).

In FIG. 3, the in-vitro dissolutions of Examples 4–5 and 7–8 are determined as per the Examples above, and compared to the dissolution of the bupivacaine free base and the bupivacaine hydrochloride salt forms. As can be seen from the graph of FIG. 3, when compared to pure bupivacaine base, each of Examples 4–5 and 7–8 showed a distinct retarding effect in their dissolution profile. Furthermore, all four examples of the invention displayed a small initial burst of drug release which was more pronounced in the microspheres prepared by the spray-dried process as compared to the examples prepared by the solvent extraction process.

Scanning electron micrographs of the microspheres for the formulations prepared by the solvent extraction and by the spray-dried technique are then compared. The spray-dried process yields microspheres which are smaller than with the solvent extraction process.

Figure 4:
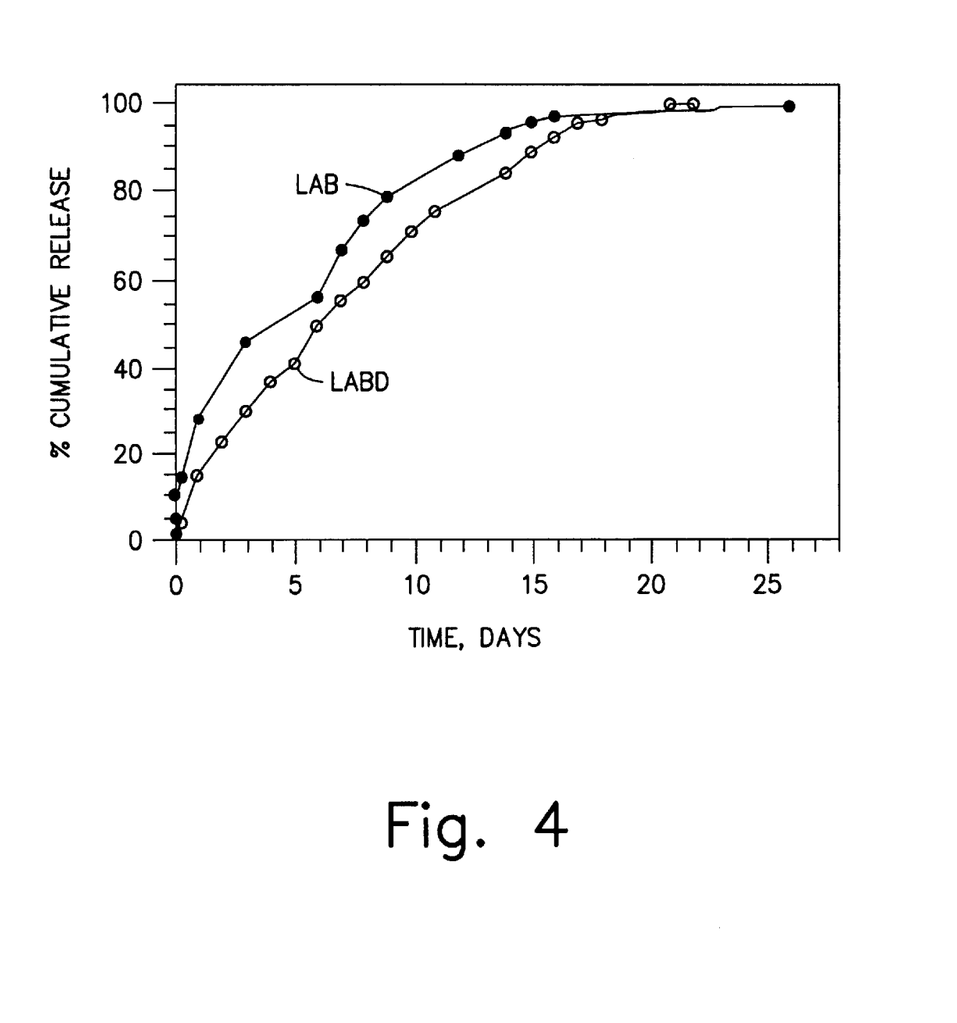
FIG. 4 is a graphical representation of the bupivacaine release rate from PLA 100, PLGA 65:35 and 75:25.

Example 10 In Vitro Release Characteristics of Bupivacaine from Microspheres Studies were carried out in vitro to monitor the rate of release of bupivacaine from the 65:35 PLGA, 75:25 PLGA and PLA 100 microspheres loaded with bupivacaine from about 70% to about 75% (w/w). Release experiments were carried out in vitro in stirred, buffered physiological saline, the buffer being changed at the points indicated on the accompanying graph (FIG. 4). The amount of bupivacaine in each of the supernatants, was quantitative spectrophotometrically. In some experiments, release of tritiated bupivacaine was quantitated. Generally, the PLA 100 microspheres released the bupivacaine most rapidly, with about 90% release attained in less than 1 day. PLGA 75:25 and 65:25 microspheres reached about 80% release after about 10 days, as illustrated by FIG. 4.

Example 11 Pharmacodynamics of Anesthesia in Response to Lab

Methods
Rat Hot Plate Assay

Rats were anesthetized with halothane during drug administration. Microsphere preparations were injected in 0.6 ml using an 18 gauge needle, proximal to the sciatic nerve, using anatomic landmarks. Data are presented as latency. Latency refers to the amount of time an animal voluntarily leaves its paw on the hot plate (maintained at 56 C.), about 2 seconds in a normal animal. In animals experiencing local anesthesia, paws are removed from the hot plate after 12 seconds by the experimenter to avoid tissue damage.

Results

Dose-response studies were performed using 50–600 mg/kg body weight bupivacaine. It was determined that doses as high as 600 mg/kg can be administered, with transient decreased activity as the only observable side effect at the highest dose.

Example 12 Preparation of Microspheres with Bupivacaine at Greater Than 70% Loading by Weight Materials Microspheres with bupivacaine free base loaded at greater than 70% by weight, were prepared by a process using the materials provided by Table 3, below, in the indicated proportions.

TABLE 3

Materials For Preparation of High Load Bupivacaine Microspheres

| Component | Wt % of batch | Wt (g)/batch | Final % | Final (g) | Final mg/dose |
|---|---|---|---|---|---|
| Bupiv. base | 1.460E−03 | 1.080E+00 | 72.00 | 108.0 | 50.0 |
| 65:35 high iv PLGA | 5.677E−02 | 4.200E+1 | 28.00 | 42.0 | 19.4 |
| Polyvinyl alcohol | 4.055E−02 | 3.000E+01 | ** | ** | ** |
| Tris HCl | 2.181E−01 | 1.613E+2 | ** | ** | ** |
| Tris base | 4.303E−01 | 3.183E+02 | ** | ** | ** |

TABLE 3-continued

Materials For Preparation of High Load Bupivacaine Microspheres

| Component | Wt % of batch | Wt (g)/batch | Final % | Final (g) | Final mg/dose |
|---|---|---|---|---|---|
| Ethyl acetate | 1.511E+00 | 1.118E+03 | ** | ** | ** |
| Purified H$_2$O | 9.774E+01 | 7.23E+04 | ** | ** | ** |
| TOTAL | 1.000E+2 (100%) | 7.398E+4 (7398 g) | 100.0 | 150.0 | 69.4 |

** Removed during processing.

Equipment

The stock solutions for the preparation of the microspheres were prepared with standard laboratory equipment, e.g., beakers and mixers. The final mixing of the organic phase and aqueous phase solutions and quenching, was conducted in an apparatus having a temperature regulated circulating water bath, and at least two reactor vessels for holding the organic and aqueous phase solutions, of 2 and 3 liters, respectively, and a quench tank. The reactor vessels (or simply "reactors") was each equipped with a mixing propeller. The apparatus also included a static mixer and gear pump for each reactor.

Process

The high load bupivacaine containing microspheres were prepared as follows.

A. Preparation of 65:35 Organic Phase Polymer Solution

Ethyl acetate (937.5 g) was added to a 2 liter beaker followed by the addition of 42.00 g of 65:35 PLGA with moderate mixing. The container was covered and moderate ring continued until a clear solution was formed.

B. Preparation of Polyvinyl Alcohol/Tris Buffer Aqueous Solution

Polyvinyl alcohol (PVA; 600 g) was added to a 4 liter beaker and then diluted with 2201 g purified water followed by stirring. Thereafter 6.63 g Tris HCl and 13.08 g Tris base were added with stirring until the solution was clear, then the stirring was halted and the beaker covered. The buffer solution had a measured pH of about 8.47.

C. Preparation of Quench Media

A quench tank was filled with 69.54 kg of purified water. The quench tank propeller mixer was run at a moderate speed and 154.7 g Tris HCl and 305.2 g Tris base were added to the quench tank with stirring, until a clear solution was formed. The quench media had a measured pH of about 8.50.

D. Completing Preparation of Organic Phase by Adding Bupivacaine

The weight of the organic phase polymer solution prepared at step A above was adjusted to 975.0 g as required and the polymer solution was transferred to a 2 liter temperature regulated reactor and 108 g of bupivacaine base was added to the organic phase polymer solution with stirring by a built in propeller.

E. Completing Preparation of Aqueous Phase by Adding Ethyl Acetate

Ethyl acetate, 180.0 g was added to the polyvinyl alcohol Tris buffer of step B, above, with about 2 minutes of moderate stirring by a built in propeller. The stirred aqueous phase solution was transferred to a 3 liter temperature regulated reactor.

F. Mixing and Quenching of the Organic and Aqueous Phases

The propeller in the quench mixing tank was placed at an angled position about 8 cm from the bottom of the tank and activated to about 800 cpm. The outlet tube of the static mixer was positioned below the propeller mixing blades of the quench tank, the propeller mixer was turned off and the pumping of the aqueous phase through the static mixer was commenced. The flow of the organic phase through the static mixer was established through the static mixer, which took about 10.1 minutes to drain the organic phase reactor, at which time the organic phase pump was turned off. The aqueous phase pumping continued through the static mixer for rinsing until all of the aqueous phase was exhausted, at which time the aqueous phase pump was shut down. The quench phases was, then stirred for about one hour after the organic phase, reactor is emptied.

G. Microsphere Collection, Sieving and Drying

A peristaltic pump was used to pump suspended microspheres through stacked sieves, two 25 micron sieves and two of 135 microns. Each sieve collection was then rinsed with about 2 liters of purified water. About 231.5 g of wet microspheres were collected from the 25 micron sieves and about 92 g of wet microspheres were collected from the 125 micron sieves. After drying at room temperature overnight and removal from the sieves, the yield was about 110 g of microspheres from the 25 micron sieves and about 16.7 g of microspheres from the 125 micron sieves. The microspheres were then further treated by drying at about 18.5–18.8 C., in a Vacuum oven, followed by a final screening through a 125 micron sieve.

H. Bupivacaine Content Confirmed

The microspheres so produced were assayed for bupivacaine content by standard methods, which was determined for the batch produced as described above as 72.00 percent bupivacaine and 28.99 percent 65:35 high iv PLGA or 50.00 mg bupivacaine per dose and 19.44 mg/dose of the PLGA.

I. Multiple Batches were Pooled

Multiple batches of microspheres were prepared as described above and the so obtained microspheres pooled to provide the microspheres for the safety determinations described herein.

Example 13 Single Dose Toxicity in Rats

Methods

Sprague-Dawley rats from Charles River, 6–8 weeks of age (body weight about 15–200 grams for females and about 200–290 grams for males) were used for these studies.

Male and female rats were dosed intramuscularly in the hind limb with bupivacaine base (the form used in the microspheres), aqueous bupivacaine HCl, or LAB. The animals were examined for pharmacotoxic signs (including tremors and convulsions, and death).

Results

The results of the intramuscular study are summarized in Table 4, below. These data indicate that LAB has an excellent safety margin versus bupivacaine free base, for example, after intramuscular dosing, the lowest lethal dose of bupivacaine hydrochloride was 10.6 mg/kg, whereas no toxic effects were found in rats given up to 400 mg/kg LAB. Temporary paralysis of the hindlimb was observed in animals dosed with bupivacaine in microspheres (local motor anesthesia). More transient paralysis was observed after administration of aqueous bupivacaine hydrochloride. This is a reflection of the expected pharmacology of bupivacaine.

TABLE 4

Summary of acute lethality studies in rats given intramuscular (I.M.) doses of bupivacaine HCl, bupivacaine free base or bupivacaine containing microspheres ("LAB").

| Dose, mg/kg | Bupivacaine HCl Mortality | Bupivacaine free base Mortality | LAB** (free base) Mortality |
|---|---|---|---|
| 5 | 0/4 | 0/4 | — |
| 10 | 0/4 | 0/4 | — |
| 25 | 0/4 | 0/4 | — |
| 50 | 4/4 | 1/4 | 0/4* |
| 100 | 4/4 | 1/4 | 0/4 |
| 150 | — | 2/4 | 0/4 |
| 200 | — | — | 0/4 |
| 250 | — | — | 0/4 |
| 300 | — | — | 0/4 |

All deaths occurred 10–30 minutes post-dosing
*1/4 with seizures
**LAB is long acting bupivacaine (microspheres).

Therefore, the data of Table 4 confirm that the methods and formulations according to the invention provide a safer local anesthesia than has heretofore been available.

CONCLUSION

The present invention is not to be limited in scope by the specific embodiments described herein. Indeed, various modifications of the invention in addition to those described herein will become apparent to those skilled in the art from the foregoing description. Such modifications are intended to fall within the scope of the claims. Various publications are cited herein, the disclosures of which are incorporated by reference in their entireties.

What is claimed is:

1. A method for providing local anesthesia at a site in a patient, comprising:
administering at a site in a patient in need thereof a dose of biocompatible, biodegradable, controlled release microspheres consisting essentially of bupivacaine incorporated at a percent loading from about 60 to about 90% in a polymeric material selected from the group consisting of a polylactide, a polyglycolide, a poly (lactide-co-glycolide), a polyanhydride, a polyorthoester, a polycaprolactone, a polyphosphazene, a polysaccharide, a proteinaceous polymer, a soluble derivative of a polysaccharide, a soluble derivative of a proteinaceous polymer, a polypeptide, a polyester, a polyorthoester, and mixtures thereof contained in a pharmaceutically acceptable carrier, said dose providing local anesthesia to said site for a period of one day, said bupivacaine being present in said dose in an amount effective to induce a localized condition selected from the group consisting of sensory anesthesia, motor anesthesia and combinations thereof, and said dose providing local anesthesia having substantially improved safety relative to a formulation providing a pharmaceutically equivalent effect of bupivacaine administered in immediate release form.

2. The method of claim 1, wherein at least a portion of the dose of said bupivacaine is in immediate release form.

3. The method of claim 1, wherein said dose is a plurality of controlled release microspheres suspended in a pharmaceutically acceptable medium for injection, and said method comprises injecting a pharmaceutically effective dose of said microspheres at the site.

4. The method of claim 1, wherein said step of administering said dose comprises injecting or implanting said formulation in proximity to a nerve to be anesthetized.

5. The method of claim 3, wherein the bupivacaine is incorporated into said plurality of controlled release microspheres at a percent loading from about 70% to about 75% by weight.

6. The method of claim 1, wherein said bupivacaine is selected from the group consisting of bupivacaine free base, bupivacaine hydrochloride, and any salts, derivatives or mixtures thereof.

7. The method of claim 3, wherein the bupivacaine is incorporated into said plurality of controlled release microspheres at a percent loading from greater than 70% to about 90% by weight.

8. The method of claim 1, wherein said local anesthetic is bupivacaine HCL.

9. The method of claim 6, wherein said local anesthetic is bupivacaine free base.

10. The method of claim 1, wherein the bupivacaine is administered in a dose ranging from 5 through 450 mg/kg of a patient.

11. The method of claim 1, wherein said dose, when injected into the patient intravenously, fails to induce a toxic reaction.

12. The method of claim 11, wherein the intravenously administered dose of the biocompatible, biodegradable, controlled release microspheres results in a bupivacaine blood plasma level of less than 1600 ng/ml in the patient.

13. The method claim 11, wherein the intravenously administered dose of the biocompatible, biodegradable, controlled release microspheres results in a bupivacaine blood plasma level of less than 1200 ng/ml in the patient.

14. The method of claim 11, wherein the intravenously administered dose of the biocompatible, controlled release microspheres is unable to produce a bupivacaine blood plasma level of higher than from about 200 to about 650 ng/ml in the patient.

15. The method of claim 1, wherein the polymeric material has a molecular weight of from about 5,000 to about 200,000.

16. The method of claim 1, wherein the microspheres comprising bupivacaine further comprises a glucocorticoid.

17. The method of claim 1, wherein said dose of microspheres is a plurality of controlled release microcapsules suspended in a pharmaceutically acceptable medium for injection, and said method comprises injecting a pharmaceutically effective dose of said microcapsules at the site.

18. The method of claim 6, wherein the dose of said bupivacaine administered is 1–100 mg per nerve.

19. The method of claim 1, wherein the polymeric material is a poly (lactide-co-glycolide) wherein the mole percent composition of lactide and glycolide is 50% lactide and 50% glycolide.

20. The method of claim 1, wherein the polymeric material is a poly (lactide-co-glycolide) wherein the mole percent composition of lactide and glycolide is 65% lactide and 35% glycolide.

21. The method of claim 1, wherein the polymeric material is a poly (lactide-co-glycolide) wherein the mole percent composition of lactide and glycolide is 75% lactide and 25% glycolide.

22. The method of claim 1, wherein the polymeric material is a poly (lactide-co-glycolide) wherein the mole percent composition of lactide and glycolide is 85% lactide and 15% glycolide.

23. The method of claim 3, wherein the bupivacaine is incorporated into said microspheres at a percent loading from about 60% to about 80%, by weight.

24. The method of claim 3, wherein the bupivacaine is incorporated into said microspheres at a percent loading from about 70% to about 90%, by weight.

25. A method for providing local anesthesia at a site in a patient, comprising:
administering at a site in a patient in need thereof a dose of controlled release microspheres consisting essentially of bupivacaine incorporated at a percent loading from about 60 to about 90% in a biocompatible, biodegradable, polymeric material contained in a pharmaceutically acceptable carrier, said dose providing local anesthesia to said site for a period of one day, said bupivacaine being present in said dose in an amount effective to provide analgesia or anesthesia at the site, said dose providing local anesthesia having substantially improved safety relative to a formulation providing a pharmaceutically equivalent effect of bupivacaine administered in immediate release form.

26. A method for providing local anesthesia at a site in a patient, comprising:
administering at a site in a patient in need thereof a bupivacaine formulation consisting essentially of a plurality of controlled release microcapsules containing a therapeutically effective amount of bupivacaine free base incorporated at a percent loading from about 60 to about 90% in a biocompatible, biodegradable, polymeric material consisting essentially of a copolymer of lactic acid and glyco lie acid, said formulation providing local anesthesia to said site for a period of one day, said bupivacaine being released from said microcapsules when administered at the site at a rate sufficient to provide analgesia or anesthesia at the site, said formulation having substantially improved safety relative to a formulation providing a pharmaceutically equivalent effect of said bupivacaine administered in immediate release form.

27. A method for providing local anesthesia at a site in a patient, comprising:
administering at a site in a patient in need thereof a dose of biocompatible, biodegradable, controlled release microparticles consisting essentially of bupivacaine incorporated at a percent loading from about 60 to about 90% in a polymeric material selected from the group consisting of a polylactide, a polyglycolide, a poly (lactide-co-glycolide), a polyanhydride, a polyorthoester, a polycaprolactone, a polyphosphazene, a polysaccharide, a proteinaceous polymer, a soluble derivative of a polysaccharide, a soluble derivative of a proteinaceous polymer, a polypeptide, a polyester, a polyorthoester, and mixtures thereof, contained in a pharmaceutically acceptable carrier, said dose providing local anesthesia to said site for a period of one day, said bupivacaine being present in an amount effective to induce a localized condition selected from the group consisting of sensory anesthesia, motor anesthesia and combinations thereof, and said dose providing local anesthesia having substantially improved safety relative to a formulation providing a pharmaceutically equivalent effect of bupivacaine administered in immediate release form.

* * * * *